United States Patent
Andres

(10) Patent No.: US 10,231,908 B2
(45) Date of Patent: *Mar. 19, 2019

(54) METHOD OF REDUCING HAIR LOSS ASSOCIATED WITH CHEMOTHERAPY

(71) Applicant: Galderma S.A., Lausanne Grey (CH)

(72) Inventor: Philippe Andres, Peymeinade (FR)

(73) Assignee: GALDERMA S.A., Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/844,909

(22) Filed: Dec. 18, 2017

(65) Prior Publication Data

US 2018/0104170 A1  Apr. 19, 2018

Related U.S. Application Data

(63) Continuation of application No. 15/204,506, filed on Jul. 7, 2016, now Pat. No. 9,937,117.

(60) Provisional application No. 62/190,342, filed on Jul. 9, 2015.

(51) Int. Cl.
*A61K 8/04* (2006.01)
*A61K 8/49* (2006.01)
*A61Q 7/00* (2006.01)

(52) U.S. Cl.
CPC .............. *A61K 8/046* (2013.01); *A61K 8/042* (2013.01); *A61K 8/4953* (2013.01); *A61Q 7/00* (2013.01)

(58) Field of Classification Search
None
See application file for complete search history.

(56) References Cited

U.S. PATENT DOCUMENTS

| | | |
|---|---|---|
| 6,267,972 B1 | 7/2001 | Breton et al. |
| 2011/0294730 A1 | 12/2011 | Shantha |
| 2014/0094470 A1 | 4/2014 | Graeber et al. |
| 2014/0343159 A1 | 11/2014 | Fahl |
| 2014/0371320 A1 | 12/2014 | Trogden |

OTHER PUBLICATIONS

Davis et al., "Prevention of Chemotheraphy-Induced Alopecia in Rats by CDK Inhibitors", Science, vol. 291, pp. 134-137 (2001).
Soref et al., "A New Strategy to Prevent Chemotherapy and Radiotherapy-Induced Alopecia using Topically Applied Vasoconstrictor", Int. J. Cancer, 136, 195-203 (2015).
International Search Report for corresponding International Application No. PCT/US16/41296, pp. 1-4 (Sep. 13, 2016).
Allergan (Alphagan) "Ensure You Get the Green Bottle", p. 1-4, (2013).
Dahlmann-Noor, et al., "Brimonidine and Apraclonidine as Vasoconstrictors in Adjustable Strabismus Surgery", Jouma of AAPOS, 13:123-126 (2009).
Mayo Clinic, "Chemotherapy and Hair Loss: What to Expect During Treatment", p. 1-5, published Apr. 2004, republished Apr. 5, 2016.
KidsHealth, "Hair Loss Due to Chemotherapy" (https://www.kidshealth.org.nz), p. 1-2, Dec. 21, 2010.

*Primary Examiner* — Umamaheswari Ramachandran
(74) *Attorney, Agent, or Firm* — Sunit Talapatra; Foley & Lardner LLP

(57) ABSTRACT

A method of reducing hair loss (alopecia) in a patient undergoing or scheduled to undergo chemotherapy is claimed. The method involves administering brimonidine or a pharmaceutically acceptable salt thereof to the site of the hair follicles.

7 Claims, 3 Drawing Sheets

Control
CYP + vehicle control for brimonidine
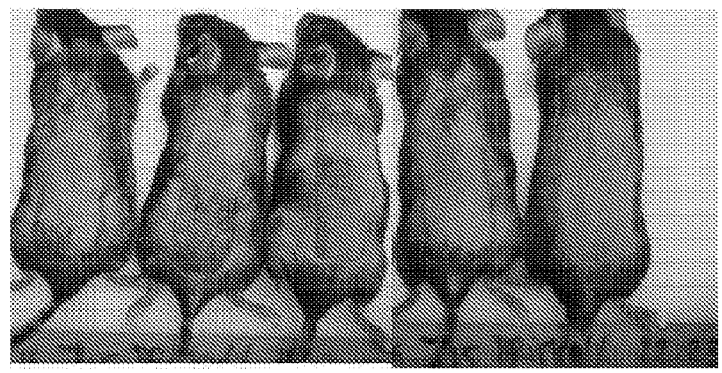
CYP + brimonidine 35 mM (1%)
FIG. 4 Day 15 post depilation

METHOD OF REDUCING HAIR LOSS ASSOCIATED WITH CHEMOTHERAPY

CROSS REFERENCE TO RELATED APPLICATIONS

This application is a continuation of U.S. application Ser. No. 15/204,506, filed on Jul. 7, 2016 which claims priority from U.S. Provisional Application Ser. No. 62/190,342, filed on Jul. 9, 2015, both of which are incorporated herein by reference.

BACKGROUND OF THE INVENTION

Cancer treatments have improved greatly throughout the past century with the development of various therapies including surgery, radiation, hormone therapy, chemotherapy, and immunotherapy. Chemotherapy remains one of the most common treatments for cancer. New chemotherapy drugs and combination chemotherapy drug regimens are constantly being developed and tested to increase potency and reduce side-effects. However, hair loss (alopecia) remains an important concern for people undergoing traditional chemotherapy.

Hair loss commonly occurs in patients undergoing chemotherapy because while chemotherapy drugs target rapidly growing cancer cells, the drugs also affect other rapidly growing cells such as the cells in the hair follicles. As a result, chemotherapy often causes a patient's hair to fall out individually and/or in clumps.

Scalp hypothermia or cryotherapy has been used with varying degrees of success to reduce hair loss. During chemotherapy, ice packs or cooling packs are applied to the patient's head in order to slow blood flow to the scalp. However, the ice packs can be uncomfortable and cause headaches.

There is a need for new methods of reducing hair loss in patients undergoing traditional chemotherapy that are easier to administer than ice and cooling packs, have less side effects, and are more effective.

SUMMARY OF INVENTION

In one embodiment, the invention relates to a method of reducing hair loss in a patient undergoing chemotherapy. The method involves topically applying a pharmaceutical composition including an effective amount of brimonidine or a pharmaceutically acceptable salt thereof to the hair follicles of the patient during the course of the chemotherapy.

The pharmaceutical composition includes a pharmaceutical carrier selected from a foam, conditioner, hair spray, shampoo, gel, cream, emulsion, or solution. Preferably, the pharmaceutical composition is a foam, conditioner, or hair spray.

The brimonidine or pharmaceutically acceptable salt thereof is preferably present in an amount of from about 0.05% by weight to about 5% by weight of the composition. More preferably, the brimonidine or pharmaceutically acceptable salt thereof is present in an amount of from about 0.05% by weight to about 2% by weight of the composition.

In another embodiment, the invention relates to a method of reducing hair loss in a patient scheduled to undergo chemotherapy. The method involves topically applying a pharmaceutical composition including an effective amount of brimonidine or a pharmaceutically acceptable salt thereof to the hair follicles of the patient prior to undergoing the chemotherapy.

In a preferred embodiment, the pharmaceutical composition is applied three to four hours before the patient is scheduled to undergo chemotherapy.

DESCRIPTION OF THE DRAWINGS

FIG. 4 Day 15 representative pictures of the dorsal depilated area of the i.p. injection of sterile water (control) or cyclophosphamide (CYP) injected mice and topically brimonidine or vehicle treated mice. On day 15 after depilation, more hairs did not shed in the brimonidine-treated mice.

DETAILED DESCRIPTION

Figure 1:
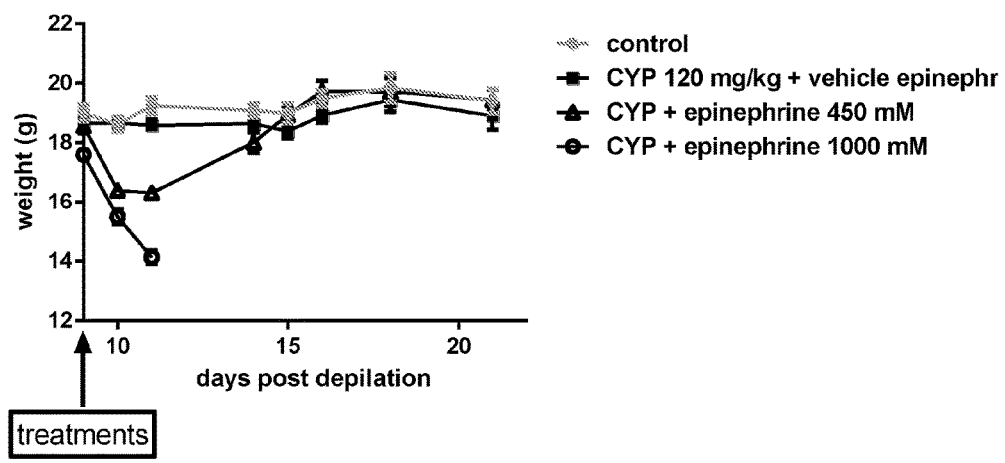
FIG. 1 Mean+/−SEM (standard error of the mean) of body mice weight after the epinephrine and cyclophosphamide treatments at day 9 of the experiment. Epinephrine 1000 mM was toxic to mice (mice were humanely euthanized at day 11), and the 450 mM dose temporarily decreased the body weight of mice.

The invention relates to a method of reducing hair loss in a patient scheduled to undergo chemotherapy or undergoing chemotherapy involving topical administration of a pharmaceutical composition including brimonidine or a pharmaceutically acceptable salt thereof to the hair follicles of the patient before, during, and/or after the course of the chemotherapy.

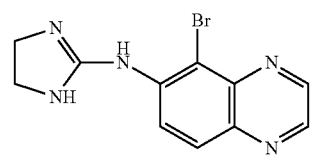

Brimonidine

Pharmaceutically acceptable salts are well known in the art. Pharmaceutically acceptable salt means those salts of brimonidine that are safe and effective for topical use in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. Pharmaceutically acceptable salts are discussed in BERGE ET AL., 66 J. PHARM. SCI. 1-19 (1977), incorporated herein by reference.

The most preferred pharmaceutically acceptable salt of brimonidine is brimonidine tartrate.

Pharmaceutical compositions include any formulations which are pharmaceutically acceptable for topical delivery of the compounds of the invention. The choice of topical formulation will depend on several factors, including the physiochemical characteristics of the particular compound(s) of the invention and of other excipients present, their stability in the formulation, available manufacturing equipment, and cost constraints.

The pharmaceutically acceptable composition is applied locally to the site of the hair follicles of the patient in any conventional manner well known in the art. For example, the composition may be applied to the scalp in a foam (mousse) composition.

The amount of brimonidine or a pharmaceutically acceptable salt thereof applied to the skin is any amount that is effective in reducing hair loss due to chemotherapy. Generally the minimum amount of brimonidine or a pharmaceutically acceptable salt thereof in a topical formulation of the invention applied to the affected skin area is about 0.0001 g/cm$^2$, preferably about 0.001 g/cm$^2$ of skin surface area. The maximum amount of brimonidine or a pharmaceutically acceptable salt thereof in a topical formulation of the invention applied to the affected skin area is about 0.05 g/cm$^2$ to about 0.008 g/cm$^2$ of skin surface area. Typically, one to four applications per day are recommended during the term of treatment.

Dosages and dosing frequency will be determined by a trained medical professional depending on the activity of the compound of the invention, the characteristics of the particular topical formulation, and the general physical condition of the person being treated.

For example, the pharmaceutical composition may be applied before, during, and/or after the course of the chemotherapy. An appropriate time before and after the course of chemotherapy may be determined by a trained medical professional. For example, a doctor may prescribe application of the composition three to four hours prior to the administration of the chemotherapy, during the course of the chemotherapy, and in the five days after the administration of the chemotherapy. In another example, a doctor may prescribe administration of the composition a day before administration of the chemotherapy.

In general, brimonidine or a pharmaceutically acceptable salt thereof is present in a formulation of the invention in a minimum amount of from about 0.05 percent, about 0.1 percent, or about 0.15 percent of the total weight of the formulation. Preferably, brimonidine or a pharmaceutically acceptable salt thereof is present in a formulation of the invention in a maximum amount of about 5 percent, about 2 percent, about 1 percent, or about 0.5 percent of the total weight of the formulation.

It is to be understood that the present invention contemplates embodiments in which each minima is combined with each maxima to create all feasible ranges. For example, brimonidine or a pharmaceutically acceptable salt thereof may be present in a composition of the invention in an amount of from about 0.05 percent to about 1 percent based upon the total weight of the composition or likewise from about 0.1 percent to about 1 percent based upon the total weight of the composition.

In one embodiment, the compounds of the invention are delivered to the affected area of the skin in a pharmaceutically acceptable topical carrier. As used herein, a pharmaceutically acceptable topical carrier is any pharmaceutically acceptable formulation that can be applied to the skin surface for topical or dermal delivery of a pharmaceutical or medicament. The combination of a pharmaceutically acceptable topical carrier and a compound of the invention is termed a pharmaceutical composition of the invention. Pharmaceutical compositions of the invention are prepared by mixing a compound of the invention with a topical carrier according to well-known methods in the art, for example, methods provided by standard reference texts such as, REMINGTON: THE SCIENCE AND PRACTICE OF PHARMACY 1577-1591, 1672-1673, 866-885 (Alfonso R. Gennaro ed. 19th ed. 1995); Ghosh, T. K.; et al. TRANSDERMAL AND TOPICAL DRUG DELIVERY SYSTEMS (1997), both of which are hereby incorporated herein by reference. The discussion of pharmaceutical compositions containing alpha adrenergic receptor agonists from U.S. Pat. No. 7,439,241 is incorporated herein by reference.

The topical carriers useful for topical delivery of compounds of the invention can be any carrier known in the art for topically administering pharmaceuticals, for example, but not limited to, pharmaceutically acceptable solvents, such as a polyalcohol or water; emulsions (either oil-in-water or water-in-oil emulsions), such as creams or lotions; micro emulsions; gels; ointments; liposomes; powders; and aqueous solutions or suspensions. The preferred carriers are foams (mousse), conditioners, hair sprays, shampoos, gels, creams, emulsions, and solutions.

EXAMPLES

Example 1

| Foam (Mousse) Composition | |
|---|---|
| Ingredient | Weight Percent |
| Brimonidine tartrate | 0.25% |
| Solubilizer | 2% |
| Fragrance | 0.5% |
| Cocamine DEA | 2% |
| PVP/VA Copolymer | 5% |
| Silicone Quaternium-16 (and) Undeceth-11 (and) Butyloctanol (and) Undeceth-5 (Dow Corning 5-7113 Silicone Quat Microemulsion) | 4% |
| Preservative | 0.5% |
| Cocamidopropyl Betaine | 2% |
| PEG-12 Dimethicone (Xiameter OFX-0193 Fluid) | 1% |
| Water | QS |
| TOTAL | 100% |

Example 2

| Hair Spray | |
|---|---|
| Ingredient | Weight Percent |
| Brimonidine tartrate | 0.18% |
| Ethanol | 47.02% |
| Acrylates/Hydroxyesters Acrylates Copolymer (ACUDYNE DHR) | 7.6% |
| Acrylates/C1-2 succinates/Hydroxyacrylates Copolymer (ACUDYNE LT-120) | 7.5% |
| Aminomethyl Propanol (AMP Ultra PC-2000) | 1.2% |
| PEG-12 Dimethicone (Dow Corning 193 Fluid) | 1.0% |
| MEA Borate and MIPA Borate (Monacor BE) | 0.3% |
| Fragrance | 0.2% |
| Dimethyl ether (Dymel A) | 20.0% |
| Isobutane | 15.0% |
| TOTAL | 100% |

Example 3

| Gel Composition | |
|---|---|
| Ingredient | Weight Percent |
| Brimonidine tartrate | 0.33% |
| Oxymetazoline hydrochloride | 0.2% |
| Carbomer 934P | 1.25% |
| Methylparaben | 0.3% |
| Phenoxyethanol | 0.4% |
| Glycerin | 5.5% |
| 10% Titanium dioxide | 0.625% |
| Propylene glycol | 5.5% |
| 10% NaOH Solution | 6.5% |
| DI Water | QS |
| TOTAL | 100% |

Example 4

| Cream Composition | |
|---|---|
| Ingredient | Weight Percent |
| Brimonidine tartrate | 0.5% |
| Oxymetazoline hydrochloride | 0.5% |
| Phenoxyethanol | 0.8% |
| Methylparaben | 0.2% |
| Propylparaben | 0.05% |
| Disodium EDTA | 0.01% |
| Butylated Hydroxytoluene | 0.05% |
| PEG-300 | 4.0% |
| PEG-6 Stearate (and) Glycol Stearate (and) PEG-32 Stearate | 7.5% |
| Cetostearyl alcohol | 4.0% |
| Caprylic capric triglycerides | 7.0% |
| Diisopropyl adipate | 7.0% |
| Oleyl alcohol | 7.0% |
| Lanolin USP | 2.0% |
| Ceteareth-6 (and) Stearyl Alcohol | 2.0% |
| Ceteareth-25 | 2.0% |
| Tartaric Acid | 0.001% |
| DI Water | 55.389% |
| TOTAL | 100% |

Example 5

A mousse containing 0.20 weight % brimonidine tartrate is administered to the scalp of a patient undergoing chemotherapy. The patient applies one golf-ball sized dose of mousse to her scalp after shampooing the night before she is scheduled to undergo chemotherapy. She also applies a similar dose to her scalp after daily shampooing on the day she receives chemotherapy. She continues this dosing routine throughout the course of her chemotherapy in order to prevent hair loss.

Example 6

A patient applies a golf-ball sized dose of mousse containing 0.33 weight % brimonidine tartrate to her scalp four hours before undergoing chemotherapy. She continues applying the mousse to her scalp once a day throughout the course of the chemotherapy and four days after the end of the chemotherapy.

Example 7

Figure 2:
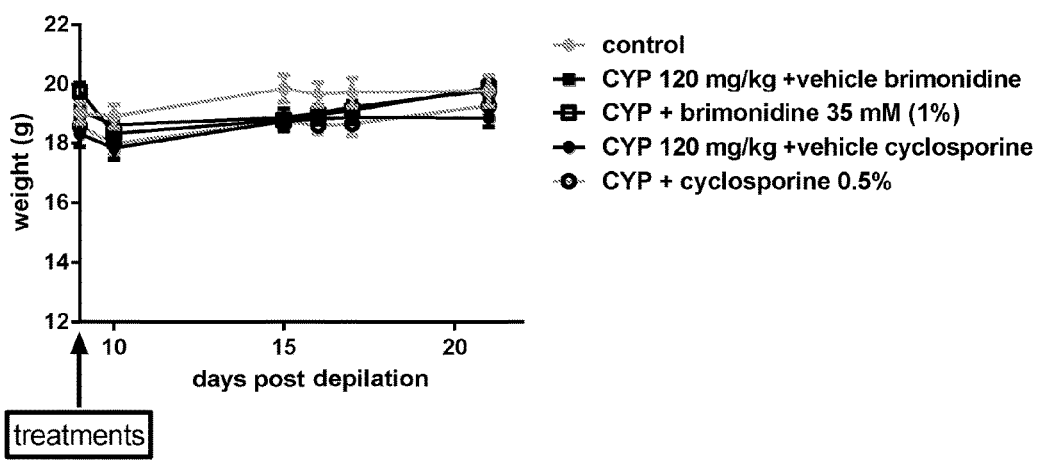
FIG. 2 Mean+/−SEM of body mice weight after the brimonidine or cyclosporine and cyclophosphamide (CYP) treatments at day 9 of the experiment. No toxic effect at 35 mM was observed for brimonidine.
Figure 3:
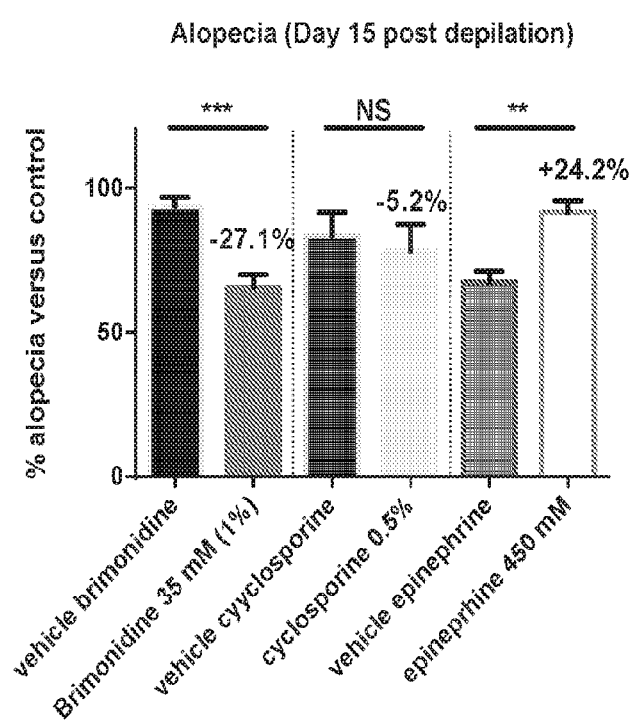
FIG. 3 % of alopecia+/−SEM versus control (control=vehicle treatment by topical way and i.p. (intraperitoneal) injection of sterile water at day 9) on day 15 after anagen induction and 6 days after CYP injection. Day 15 corresponds to the initial follicle response phase to chemical injury. Brimonidine treatment at 35 mM (1%) prevents alopecia in mice (N=8), in contrast to epinephrine 450 mM that worsened it (N=9). Cyclosporine was used as control in this experiment. The level of significance was calculated by the non-parametric Mann-Whitney test for unpaired samples.

Experiments were carried out on mice in which a portion of their backs was shaved, i.e., depilated. The experiments compared the effects on hair growth of mice administered CYP (cyclophosphamide, a chemotherapy drug with alopecia as a side effect) and a vehicle control for brimonidine; CYP and brimonidine; and a control. See FIG. 4. The mean weight of the mice was also compared following treatment with CYP and a vehicle control for epinephrine; CYP and epinephrine at two doses; CYP and a vehicle control for brimonidine; CYP and brimonidine; CYP and a vehicle control for cyclosporine; and CYP and cyclosporine for a preliminary determination of toxicity of the treatments. See FIGS. 1 and 2. The percentage of alopecia 15 days after depilation was also determined. See FIG. 3.

Material and Method

The animals used are 5-week-old female C57B16 mice obtained from Janvier labs (L'Arbresle, France) and were maintained on 12 hr light/dark cycle and provided ad. lib. water and lab chow. All animal procedures were performed in accordance with the described procedure approved by Sanofi's ethical committee (CEPAL) in agreement with the French regulation and the AAALAC certification.

Cyclophosphamide (Cytoxan, #C7397) in solution in sterile water, 100 mg/mL, Epinephrine hydrochloride (LOPAC®>98% purity, E4642) were obtained from SIGMA. Brimonidine tartrate was supplied by Galderma. The vehicle control for brimonidine and epinephrine was PEG400/EtOH100/NaCl0.9% (30/20/50) and for cyclosporine was ethanol.

At day 1, the mice were weighed and a 10 cm² skin area on their backs was shaved. From day 2 to day 24: mice were observed daily and mouse body weight was monitored every 2-3 days in addition to the depilated area observation. At day 9 postdepilation, cyclophosphamide (CYP) in solution in sterile water was administered by i.p. injection at the final dosage of 120 mg/kg (10 mL/kg) to all animals except for the control group mice.

Nine days after anagen induction by depilation, the vehicles (day 9), brimonidine at 35 mM (1%), epinephrine at 450 mM (10.5%) or 1000 mM (21.9%) or cyclosporine at 0.5%, 100 µL each, were administrated on the back of mice following these schedule treatments:

Brimonidine treatment: based on preliminary pharmacokinetic data of brimonidine penetration in mouse skin, vehicle or brimonidine was first administered (t-2 hours) and cyclophosphamide 120 mg/kg was injected i.p. 2 hours after that administration. Topical application of brimonidine or vehicle was repeated 2 hours after the first application to allow a good exposure of the skin in order to cover the plasmatic half-life of cyclophosphamide in mice (Said et al., "Cyclophosphamine Pharmokinetics in Mice: A Comparison Between Retro Orbital Sampling Versus Serial Tail Vein Bleeding" The Open Pharmacology Journal, Vol. 1, pgs. 30-37, 2007).

Epinephrine treatment: based on the topical application schedule from the publication of Soref, et al. "A new strategy to prevent chemotherapy and radiotherapy-induced alopecia using topically applied vasoconstrictor" Int. J. Cancer, Vol. 136, pgs. 195-203, 2015, the vehicle or epinephrine solutions was applied 20 min before (t-20 min) and then 10, 40 and 60 min after cyclophosphamide 120 mg/kg i.p. administration to cover the plasmatic half-life of cyclophosphamide in mouse (Said et al., The Open Pharmacology Journal, Vol. 1, pgs. 30-37, 2007).

Cyclosporine treatment: based on the topical application schedule from the publication of Maurer et al., "Hair Growth Modulation by Topical Immunophilin Ligands" American Journal of Pathology, Vo. 150, No. 4, pgs. 1433-1441, 1997, animals were treated with daily topical applications of ethanol as control or cyclosporine solution from days 7 to 10 after anagen induction by depilation.

After treatments on day 9, the back skin of mice was examined daily for a period of 12 days for signs of alopecia, hair regrowth, skin pigmentation and the quality of hair shaft pigmentation. The scoring of coat recovery in the depilated back skin area was analyzed by 2 independent observers and the % alopecia versus control was then calculated at day 15. Day 15 corresponds to the initial response phase to chemical injury. The level of significance was calculated by the non-parametric Mann-Whitney test for unpaired samples. P values <0.05 were accepted as significant (* for p<0.05;  for p<0.01; * for p<0.001).

CONCLUSIONS

Brimonidine, topically applied, prevented hair loss in C57BL/6 mice after cyclophosphamide administration.

As the model of cyclophosphamide-induced alopecia in C57B16 mice after a synchronized anagen induction by depilation is largely described in the literature and showed to be a clinically relevant representation of the hair follicle damage observed in patients (Hendrix et al., 2005, Yoon et al., 2015), this study with brimonidine is also relevant.

Data at Day 15 (corresponding to the initial follicle response phase to chemical injury) clearly show that Brimonidine at 35 mM (1%) prevents alopecia in mice. In contrast, epinephrine 450 mM worsened alopecia and either the cyclosporine (control) or the vehicle control for brimonidine showed no modification over the induced alopecia.

I claim:

1. A method of reducing hair loss in a patient undergoing chemotherapy, the method comprising topically applying a pharmaceutical composition comprising an effective amount of brimonidine or a pharmaceutically acceptable salt thereof to hair follicles with hair of the patient during the course of the chemotherapy.

2. The method according to claim 1, wherein the brimonidine or a pharmaceutically acceptable salt thereof is brimonidine tartrate.

3. The method according to claim 1, wherein the pharmaceutical composition is selected from the group consisting of a foam, conditioner, hair spray, shampoo, gel, cream, emulsion, and solution.

4. The method according to claim 3, wherein the pharmaceutical composition is a foam, conditioner, or hair spray.

5. The method according to claim 1, wherein the brimonidine or a pharmaceutically acceptable salt thereof is present in an amount of from about 0.05% by weight to about 5% by weight of the composition.

6. The method according to claim 1, wherein the brimonidine or a pharmaceutically acceptable salt thereof is present in an amount of from about 0.05% by weight to about 2% by weight of the composition.

7. A method of reducing hair loss in a patient undergoing chemotherapy, the method comprising topically applying a pharmaceutical composition consisting of an effective amount of brimonidine or a pharmaceutically acceptable salt thereof and a pharmaceutical carrier to hair follicles with hair of the patient during the course of the chemotherapy.

* * * * *